(12) United States Patent
Ohashi

(10) Patent No.: US 8,067,176 B2
(45) Date of Patent: Nov. 29, 2011

(54) MICROCHEMISTRY REACTION METHOD

(75) Inventor: Tetsuo Ohashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 265 days.

(21) Appl. No.: 12/010,443

(22) Filed: Jan. 25, 2008

(65) Prior Publication Data

US 2009/0191594 A1 Jul. 30, 2009

(51) Int. Cl.
*C12Q 1/68* (2006.01)
*C12P 19/34* (2006.01)

(52) U.S. Cl. .................. 435/6.12; 435/6.1; 435/6.11

(58) Field of Classification Search .................. None
See application file for complete search history.

(56) References Cited

FOREIGN PATENT DOCUMENTS

| JP | 2000-111557 | 4/2000 |
|----|-------------|--------|
| JP | 2004-170127 | 6/2004 |
| JP | 2005-030987 | 2/2005 |
| JP | 2005-308668 | 11/2005 |
| JP | 2006-061031 | 3/2006 |
| JP | 2006-162264 | 6/2006 |
| WO | WO 2005/108571 | 11/2005 |

OTHER PUBLICATIONS

Lehmann et al. Angew. chem. Int. Ed. vol. 45:3062-3067. 2006.*
Ohashi et al. Biomed. Microdevices vol. 9:695-702. 2007.*
Hsieh et al. The 10th International Conference on Miniaturized Systems for Chemistry and Life Sciences. 2006.*
"A simple device using magnetic transportion for droplet-based PCR" Biomed Microdevices (2007) 9:695-702, DOI 10.1007/s10544-007-9078-y, Published online: May 16, 2007.
"Droplet-Based DNA Purification in a Magnetic Lab-on-a-Chip" Communications; DOI: 10.1002/anie.200503624; Angew. Chem. Int. Ed. 2006 45, 3062-3067.
Nature Medicine, Advance online publication; Technical Reports, "Catching bird flu in a droplet" ; Published online Sep. 23, 2007; DOI: 10.1038/nm1634.
Institute of Physics Publishing; Journal of Micromechanics and Microengineering; "Development of an enzymatic reaction device using magnetic bead-cluster handling" DOI: 10.1088/0960-1317/16/9/017; Published on Aug. 4, 2006.
"PCR by Moving A Free Droplet Over Different Temperature Zones" Institute of Bioengineering and Nanotechnology, The 10th International Conference on Miniaturized Systems for Chemistry and Life Sciences, Nov. 5-9, 2006, Tokyo, Japan.

* cited by examiner

*Primary Examiner* — Young J Kim
(74) *Attorney, Agent, or Firm* — Manabu Kanesaka

(57) ABSTRACT

A chemical reaction is conducted in a fluid of a droplet inside a reaction receptacle or on a surface of a reaction substrate. Fluctuations of a magnetic field are applied to the droplet including an aqueous solution having magnetic body particles with a hydrophilic surface, and a physical force is transmitted to the surrounding aqueous solution through the magnetic body particles. The droplet is thus moved by the physical force to conduct an operation necessary for a chemical reaction.

4 Claims, 10 Drawing Sheets

Magnetic particles displace a droplet

Magnet moves in a direction of the arrow

Magnetic particle is detached from the droplet, and a part of the droplet body is displaced together The magnet further moves

MICROCHEMISTRY REACTION METHOD

BACKGROUND OF THE INVENTION AND RELATED ART STATEMENT

The present invention relates to a micro-chemistry reaction method which mainly manipulates a droplet including particles responding to a magnetic force such as a magnetic body or particles including the above-mentioned particles by applying a magnetic field to the above-mentioned particles on a solid-phase surface or near the solid-phase surface; and execute operations such as preparative isolation, displacement, mixture, heating, and cooling of the fluid necessary for a chemical reaction.

For an efficient control and analysis of a reaction of the chemical reaction system and a minimization of the chemical reaction system, especially, a biochemical reaction system, a micro-chemical reaction system, i.e. μ-TAS (Micro Total Analysis System) structure which can be used for the screening of medical diagnostics or the development of a new medicine, an identification test in a forensic medicine field, environmental monitoring and so on, is expected. Recently, a μ-TAS device has been studied by developing a micro flow channel or valve on a silicon or glass substrate by a microfabrication technology in a semiconductor manufacturing field.

Characteristics required for the chemical reaction on a microchip such as the μ-TAS device are efficiency of the reaction and shortening of the analysis time due to the minimization; high throughput processing due to the integration; reduction of burdens on an examinee due to the reduction of the collection quantity of a specimen material; improvement of analytical precision due to automation; reduction of environmental burdens due to the control of the amount of reagent or waste fluid; and reduction of cost. On the other hand, in addition to easiness of chip manufacturing, especially, mass production; low manufacturing cost; and handling ability, reducing size and weight of the equipment for conducting the reaction and analysis are required in order to realize the device. Furthermore, low cost and higher reliability are required for the device.

A conventional μ-TAS chip is provided with the micro flow channel on the silicon or glass substrate using semiconductor manufacturing technology, and can obtain high processing accuracy and various measures of the fluid control in a micro area. However, the conventional μ-TAS chip is impractical since a peripheral device, which conducts the reaction, tends to become large-scale and complicated in addition to a difficulty to control the cost for expensive materials or high-accuracy processing. Especially, in a genetic diagnosis in a medical field which can not cause cross-contamination, the size and weight of analyzing equipment are required to be small, and the chip has to be a disposable μ-TAS chip which can conduct the reaction in a sealed atmosphere.

On the other hand, because of the expectation of the above-mentioned application, in order to reduce the manufacturing cost and be disposable, a μ-TAS chip using a resin substrate has been studied. However, when a conventional μ-TAS approach is adopted, the establishment and maintenance of the processing accuracy when a micro flow channel, micropump, valve, mixer and so on are formed by the resin substrate, are difficult to achieve, compared to the silicon or glass substrate. However, a resin chip has an excellent applicability to a bio-genic substance such as nucleic acid and protein, and a biological sample such as a body tissue or cell in addition to that raw materials thereof are affordable, so that the resin chip is very advantageous as a material for the disposable μ-TAS chip.

A technology for transporting a minute amount of liquid in a μ-TAS field has been numerously reported. As a driving method with respect to the solution sending the minute amount of liquid, a method in which liquid or gas from a drive source of a device external portion is a driving medium by a syringe-type pump; or an electrical method using an electrostatic force or dielectrophoresis have been reported.

When utilization for the biochemical reaction, especially, diagnosis in clinical medical care is considered, in many cases, the amount of the sample at the starting time of the reaction is minute. Also, in order to reduce the burdens of the examinee, the reduction of the collection quantity of the specimen materials will be furthermore required in the future, so that a micro-amount biochemical reaction system using a μ-TAS technology is required. Also, when a large-sized screening is considered, high throughput processing of the system due to integration and parallelization is required. In the conventional minimization of the biochemical reaction, the micro flow channel was built on a silicon or glass substrate, and the solution sending, distribution, mixture and the like were conducted. However, cost and labor hours for providing the microfabrication on the substrate and also pasting substrates are required, and even if a reaction chip becomes smaller, a high-accuracy operation due to an external solution sending equipment of the solution sending drive source is required, so that the overall system becomes large-scale and impractical.

On the other hand, when the reaction chip is made disposable, the development of a resinous chip is essential; however, in order to directly mold a microflow system which is designed by materials except for resin such as a silicon substrate and the like on the resin chip, it is difficult to ensure a processing accuracy of a micrometer-order, and it is required to be designed while considering the shrinkage and transformation when molded. Accordingly, there are many problems in building the micro flow channel, micro solution sending pump, and micro valve on the resin substrate, and there are also many problems in promoting mass production.

For transporting the minute amount of liquid in a droplet state, a method electrically transporting the droplet which is formed when, for example, a minute amount of oil is added to water or a minute amount of water is added to oil, has been reported. An electrostatic carrier (refer to a Japanese non-patent document 1: "International Symposium on Microchemistry and Microsystems 2001" by Tomohiro Taniguchi, et al., 2001, pp. 104-105) using an electrostatic force two-dimensionally operates various droplets, and conducts the micro chemical reaction. However, it is required to arrange a micro electrode and also provide a high-accuracy insulation processing in the device manufacturing in addition to requiring high voltage. Accordingly, it is difficult to mass produce, and costs for a disposable device are not affordable.

On the other hand, a chemical reaction operation of the droplet including the magnetic body has also been reported (refer to Japanese non-patent document 2: "Sensors and Actuators B" by Mitsuhiro Shikida, et al., 2006, Vol. 113, pp. 563-569, and patent document 3: International Patent Publication No. 05/069045). In the above-mentioned documents, the following method has been proposed. The sample material or a material connected with the sample material is connected on the surfaces of magnetic body particles beforehand, and the magnetic body particles are displaced by a magnet and united with a droplet (for example, enzyme liquid and the like) which includes the other reagent, so that a chemical reaction is conducted. However, an object of this method is promoting the reaction process of the material connected on the surface of the magnetic body by transporting the magnetic body itself. Also, a fluid control structure such as a dividing wall is provided on a glass device, and the μ-TAS chip on the resin substrate which does not require a special processing which is a problem to be resolved by this invention, has not been obtained. Therefore, the method is directed to one method of the conventional μ-TAS device, and differs from μ-TAS technology with a novel concept wherein the micro flow channel and micropump are not required, which is the intention of this invention.

As a microchip using the magnetic body particles, there is a chip extracting and purifying the nucleic acid from a sample on a substrate, and conducting a gene amplification reaction (refer to the Japanese patent document 1: Japanese Patent Publication (TOKKAI) No. 2006-61031). In this chip, the sample and magnetic body particles are filled into a refined well; the nucleic acid in the sample is attached to the magnetic body particles; and the nucleic acid is purified by displacing the magnetic body to the other refined well using fluctuations of the magnetic field. The magnetic body wherein the nucleic acid is purified is displaced to a nucleic-acid amplification well on the chip; and the magnetic body displaced to the nucleic-acid amplification well is heated by induction heating, so that the nucleic acid attached to the magnetic body is amplified. In this chip, a reaction field such as purification and nucleic-acid amplification is within the well provided in the substrate, and in order to process the above-mentioned well on the substrate, high-accuracy and complicated microfabrication is required. Even in the above-mentioned reference examples, substrate processing is required.

In addition, the reference examples have a structure specialized in a standard protocol of the gene amplification reaction, so that they cannot respond flexibly to various biochemical reaction protocols. As in the case of the Japanese non-patent document 2, this chip is based on the assumption that the example material (DNA) is attached to the surface of the magnetic body, and this is also one method of the conventional μ-TAS device. Accordingly, the chip differs from the μ-TAS technology with the novel concept wherein the micro flow channel and micropump are not required, which is the intension of this invention.

Also, there is a method of conducting a PCR (polymerase chain reaction) within the droplet by repeatedly displacing and placing the droplet formed from PCR reagent by the electrostatic transportation among multiple heated areas (refer to Japanese patent document 2: International Patent Publication No. 03/067875).

The present invention provides a method and device which do not require to place or construct a fluid control element such as a pump, valve, mixer and the like inside a reaction receptacle, which was required for a conventional μ-TAS, so that chemical reaction operations such as the solution sending, preparative isolation, mixture, dilution, agitation and temperature control of liquid can be conducted, and a possible chemical reaction after the above-mentioned operations can be conducted.

Further objects and advantages of the invention will be apparent from the following description of the invention.

SUMMARY OF THE INVENTION

The invention includes chemical reaction methods of the first (1) to the seventh (7) aspects and chemical reaction devices of the following the eighth (8) and the ninth (9) aspects.

(1) A chemical reaction method conducts a chemical reaction in the fluid of a droplet existing inside a reaction receptacle or on the surface of a reaction substrate. By providing fluctuations of a magnetic field to the droplet formed from an aqueous solution including a magnetic body particle with hydrophilic surface, the magnetic body particle transmits a physical force to the surrounding aqueous solution, transports the droplet and conducts an operation necessary for the chemical reaction.

(2) In the chemical reaction method conducting the chemical reaction according to the first aspect, the reaction receptacle or the reaction substrate includes a temperature variation area in which a temperature changes consecutively; due to the fluctuations of the magnetic field, the droplet is displaced to at least one spot inside the temperature variation area; and the chemical reaction is conducted by controlling the temperature of the droplet.

(3) In the chemical reaction method according to the second aspect, the droplet further includes nucleic acid for amplification, and the temperature variation area has a temperature necessary at least for nucleic-acid amplification. The nucleic-acid amplification is conducted by transporting the droplet to the spot adjusted to at least one temperature necessary for the nucleic-acid amplification inside the temperature variation area by the fluctuations of the magnetic field.

(4) In the chemical reaction method according to the third aspect, the nucleic acid is the nucleic acid attached to the surface of the magnetic body particle by contacting the magnetic body particle with the hydrophilic surface with a sample including the nucleic acid inside the droplet existing inside the reaction receptacle or on the surface of the reaction substrate and consisting of nucleic-acid extraction liquid for extracting the nucleic acid from the sample.

(5) The chemical reaction method according to the fourth aspect, the nucleic acid adsorbed into the surface of the magnetic body particle is further cleaned inside the droplet existing inside the reaction receptacle or on the surface of the reaction substrate and including cleaning liquid of the magnetic body particle.

(6) The chemical reaction method according to any one of the aspects (1) to (5), a droplet inclusion medium which is insoluble in the aqueous solution forming the droplet, is filled in the reaction receptacle or contacted with the surface of the reaction substrate, and the droplet is confined inside the droplet inclusion medium.

(7) The chemical reaction method according to the aspect (6), the droplet inclusion medium is a material having a melting point lower than the temperature for conducting the chemical reaction. Before conducting the chemical reaction, the droplet inclusion medium is in a solid state and fixes the droplet, and when the chemical reaction is conducted, the droplet inclusion medium is in a liquid state and can displace the droplet.

(8) A chemical reaction device comprises the reaction receptacle or reaction substrate wherein the droplet formed from the aqueous solution including the magnetic body particle with the hydrophilic surface is placed; and a magnetic field applying means for displacing the droplet by providing the fluctuations of the magnetic field to the droplet, and conducting the necessary operation for the chemical reaction.

(9) In the chemical reaction device according to the aspect (8), the reaction receptacle or the reaction substrate includes the temperature variation area in which the temperature changes consecutively, and the magnetic field applying means displaces the droplet to at least one spot inside the variation area, and controls the temperature of the droplet.

The necessary operation for the chemical reaction according to the invention indicates at least one operation among the operations of the preparative isolation, mixture, dilution and agitation of the liquid forming the droplet by displacing the droplet including the magnetic body particle due to the fluctuations of the magnetic field, and blending multiple droplets or separating a small droplet from one droplet. Moreover, the necessary operation includes a temperature control operation. The temperature control operation conducts the heating and cooling of the liquid forming the droplet by displacing and placing the droplet at the spot wherein the temperature is adjusted in the reaction receptacle or on the reaction substrate. The chemical reaction of the invention indicates a possible state as a result of the operations necessary for the chemical reaction, and does not necessarily indicate only the chemical reaction accompanied by a physical change. Furthermore, reactions for conducting chemical and biological analyses by conducting the chemical reaction, biochemical reaction, biological interaction and the like, are also included. The physical force of the invention indicates a traction force provided to the surrounding aqueous solution wherein the magnetic body particle forms the droplet.

The droplet of the invention indicates a solution mass with a spherical shape or a shape close to the spherical shape by a surface tensile force generated due to an intermolecular force of the liquid forming the droplet.

The chemical reaction method and device of the invention can conduct the chemical reaction operations such as the transfer of solution, preparative isolation, mixture, dilution, agitation and temperature control of the liquid without placing or constructing the fluid control element such as the pump, valve, mixer and the like in the reaction receptacle, or providing microfabrication such as a reaction well or micro flow channel. As a result, the chemical reaction method and device can enable to conduct the chemical reaction, biochemical reaction and biological interaction.

DETAILED DESCRIPTION OF PREFERRED EMBODIMENTS

Hereunder, the present invention will be described in detail with reference to the attached drawings.

First Embodiment

For magnetic body particles with hydrophilic surfaces, magnetic beads (hereinafter simply referred to as magnetic silica beads) which are constituent reagents of the Plasmid DNA Purification Kit MagExtractor-Plasmid manufactured by Toyobo Co., Ltd., are used. Before the following embodiments are conducted, an undiluted solution of the magnetic silica beads inside the above-mentioned kit was suspended in purified water ten times greater in its volume, and then the supernatant was eliminated by a centrifugal operation for a minute at 500×g. This procedure was repeated 5 times, and the magnetic silica beads were rinsed with the purified water. The concentration of the magnetic silica beads suspended in the purified water was adjusted so as to become 100 mg (dry)/mL of the dry weight concentration of the same beads.

Figure 1:
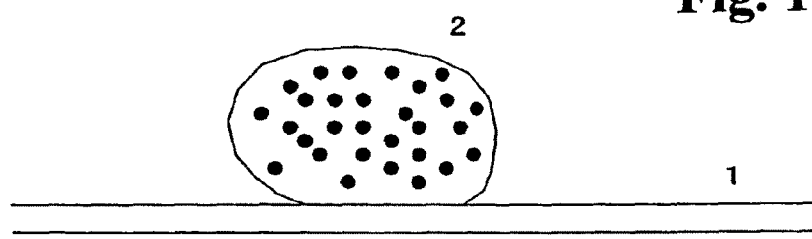
FIGS. 1(1), 1(2) are drawings showing processes of an example of a displacement method of a droplet which is a phenomenon of a basic element of the present invention, which will be explained in the first embodiment.
Figure 1:
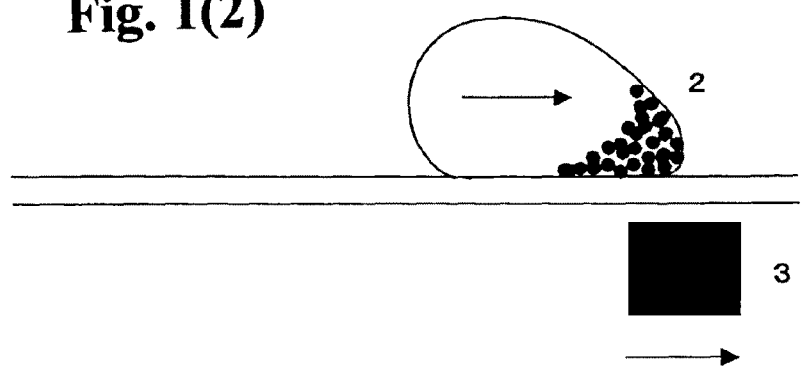

A displacement method of a droplet which becomes a basic operation of the present invention is shown in FIGS. 1(1), 1(2). For a reaction substrate, a polypropylene substrate 1 is used. FIG. 1(1) shows a state wherein liquid 10 µL with the magnetic silica beads (shown with black spots inside a droplet 2) is placed on the substrate as the droplet 2 of approximately 2.5 mm diameter in air. In the liquid, the magnetic silica beads are dispersed in purified water with the concentration of 100 mg (dry)/mL. Here, when a ferrite permanent magnet 3 is brought close to the lower side of the substrate and displaced in a horizontal direction, as shown in FIG. 1(2), the magnetic silica beads are concentrated on the right side within the droplet, and a force trying to move the whole droplet to the right side works. Surfaces of the magnetic silica beads are hydrophilic, so that when the magnetic silica beads are displaced to a direction wherein the magnet is displaced, a traction force is transmitted to water forming the droplet.

Also, on the polypropylene resin substrate with high water repellency, resistance relative to the movement between the droplet and substrate is small. Accordingly, in this condition, if the magnet is displaced at an initial speed of 10 cm per second or less, the magnetic silica beads do not overcome the surface tension of the droplet and break out of the droplet, so that the whole droplet can be displaced. In the condition, when the amount of the magnetic silica beads was retained and the droplet was enlarged further, the droplet of the maximum 200 µL (5 mg (dry)/mL of the concentration of the magnetic silica beads) could be displaced at a speed of 1 cm per second.

For the magnetic body particles with the hydrophilic surfaces (hereinafter, it is simply referred to as the magnetic body particles) which are used in the invention, materials consisting of the magnetic body such as magnetite, γ-iron oxide, manganese zinc ferrite and the like, and having the surface of hydrophilic radical such as hydroxyl group, amino group, carboxyl group, phosphate group, sulfonate group and the like, can be used including the magnetic silica beads used in the above-mentioned embodiment. For the above-mentioned magnetic body particles, more specifically, silica particles including the magnetic body; magnetic body particles whose surfaces are covered with silica; magnetic body particles whose surfaces are covered with gold including the hydrophilic radical through an SH group and the like; and gold particles including a magnetic body and whose surfaces have the hydrophilic radical through the SH group, can be used. The magnetic body particles with the hydrophilic surfaces can be taken into the droplet formed from an aqueous solution, and combined in the droplet. The droplet combined with the magnetic body particles can be easily displaced to the displacement direction of the magnetic field due to fluctuations of the magnetic field while maintaining the state of the droplet.

For an aqueous solution forming the droplet in the invention, various other aqueous solutions can be used even in the case of using only water as in the case of the above-mentioned embodiment.

When the droplet is displaced on the water repellency substrate surface such as polypropylene under an air atmosphere, the aqueous solution including alcohols such as ethanol can be also used. However, the aqueous solution including the surface tension with a level of being able to form the droplet whose diameter is approximately 5 mm and below, is preferred. More specifically, in the case of an ethanol aqueous solution, the concentration is preferred within the range of 1 (v/v)~20 (v/v) %.

Also, during the process of creating a liposome, the liposome can be treated as the droplet including the magnetic body particles in the invention by incorporating magnetic protein into a lipid membrane.

In FIGS. 1(1), 1(2), a fluctuation method of the magnetic field horizontally displaces the magnet placed on the lower side of the substrate. However, the magnet can be placed in a horizontal direction, on the upper side, or both upper and lower sides.

As a shape of a reaction receptacle, a membranous reaction receptacle wherein space surrounded by the membranes by attaching end portions of two sheets of membranes together becomes a reaction field; and a canalicular reaction receptacle such as a capillary and the like, can be cited.

The reaction substrate includes a tabular substrate; a substrate having a wall surrounding an area displacing the droplet which becomes the reaction field on the surface of the tabular substrate; and additionally, a substrate having a closed-type reaction field including a lid covering the area surrounded by the wall. The whole or a part of the lid is openable and closeable, and the droplet including the reagent or sample for conducting the chemical reaction may be able to be poured in the reaction field.

More preferably, the membranous reaction receptacle; the canalicular reaction receptacle having a flow channel whose both ends are fused and closed; and the reaction receptacle or the reaction substrate including a fully-closed-type reaction field such as the reaction substrate wherein the reaction substrate, the wall, and the lid are integrally molded, are preferably used. When the fully-closed-type reaction field is included, external contaminations can be prevented from the time wherein the chemical reaction is conducted to the time wherein a reactant is detected and analyzed. Especially, when the following nucleic-acid amplification reaction is conducted, the fully-closed-type reaction field is very effective.

On the surface of the wall inside the reaction receptacle or the reaction substrate, the surface wherein the droplet contacts when the droplet is displaced due to the fluctuations of the magnetic field is preferred to have a smooth surface. Especially, the surface roughness is preferred to be Ra=0.1 μm and below. By forming the surface roughness of Ra=0.1 μm and below, for example, when the permanent magnet is approached from the lower side of the reaction substrate and the droplet is displaced due to the fluctuations of the magnetic field, although the magnetic body particles are displaced while being pressed against the surface of the substrate, the capability to follow the displacement of the permanent magnet can be improved.

Materials for the reaction receptacle or reaction substrate are preferred to be available at a moderate price in terms of disposability and mass productivity. Also, in order to decrease the displacement resistance when the droplet is displaced, water repellency materials are preferred. As the above-mentioned materials, resin materials such as polypropylene, Teflon (registered trademark), polyethylene, polyvinyl chloride, polystyrene, and polycarbonate, can be cited.

In the above-mentioned materials, it is preferred to have optical transparency in order to be able to conduct the optical detection when absorbance, fluorescence, chemiluminescence, bioluminescence, and change of the refractive index of the droplet are measured from the outside of the reaction receptacle or the back surface of the reaction substrate.

Second Embodiment

In this embodiment, an embodiment of preparative isolation of the liquid, which is one of operations necessary for the chemical reaction, will be shown.

A moving phenomenon of the droplet by a moving magnetic field is observed as shown in the first embodiment by adjusting the volume of the droplet, the concentration of the magnetic body particles, the fluctuation method of the magnetic field and the like. On the other hand, by using a frictional force between the droplet and the wall inside the reaction receptacle or the surface of the reaction substrate, i.e. a force in which the surface of the reaction substrate tries to hold back the droplet, a part of the droplet body can be separated as a small droplet with the magnetic body particles. For example, in case the concentration of the magnetic body particles in the aqueous solution forming the droplet is low, the frictional force between the droplet and the surface of the substrate is stronger than a traction force of the magnetic body particles inside the droplet and the traction force of the magnetic body particles becomes larger than an intermolecular force between the magnetic body particles and the aqueous solution forming the droplet, the magnetic body particles are detached in the displacement direction of the magnetic field from the droplet body. At that time, the magnetic body particles are separated while bringing some part of the original droplet body around the magnetic body particles, so that preparative isolation of the liquid can be possible.

Figure 2:
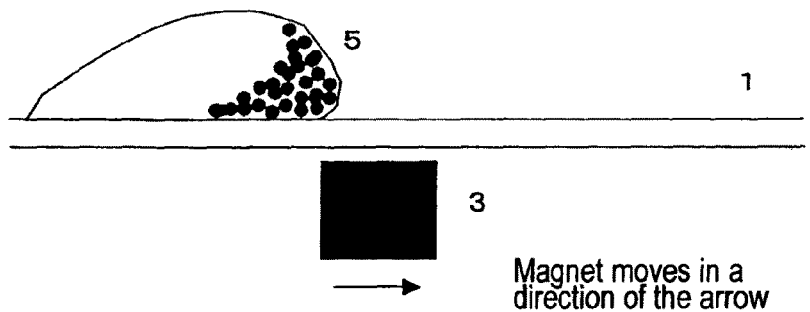
FIGS. 2(1), 2(2) are drawings showing processes of an example of a preparative isolation method of liquid according to the invention, which will be explained in the second embodiment.
Figure 2:
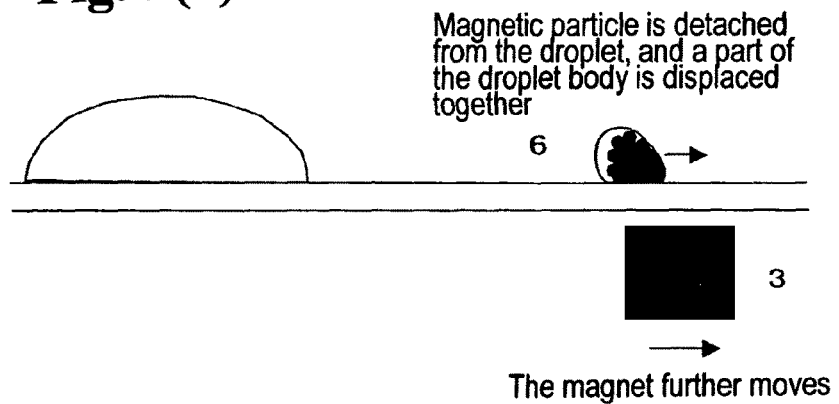

FIGS. 2(1), 2(2) show a process of the preparative isolation of the liquid by separating the small droplet from a liquid body. The drawings show the case wherein a droplet 5 consisting of the purified water of 50 μL including the magnetic silica beads (adjusted in the first embodiment) with the concentration of 2 mg (dry)/mL is placed on the surface of the polypropylene substrate 1 as the reaction substrate in the air. When the magnet 3 is displaced in a horizontal direction from the lower side of the substrate, the magnetic silica beads (shown with black spots inside the droplet) become a small droplet 6 and are separated from the droplet body. Compared to the first embodiment, the amount of the magnetic body particles is made smaller relative to the volume of the droplet, so that the above-mentioned behaviors of the magnetic silica beads are observed.

Separation of the small droplet including the magnetic body particles from the droplet including the magnetic body particles, or size of the small droplet to be separated can be repeatedly conducted by setting a parameter such as composition of the aqueous solution forming the droplet; interaction between the surface of the reaction substrate and the droplet; the concentration of the magnetic body particles; or intensity or fluctuating velocity of the magnetic field. A person skilled in the art can adjust each parameter and conduct the experiment while checking behaviors of the magnetic body particles in the droplet.

By a preparative isolation method of the liquid of the embodiment, a preparative isolation operation of quantitative liquid can be conducted repeatedly without a special process such as a depression and projection and the like, or a flow control structure such as a flow channel and the like in the reaction field of the reaction receptacle or the reaction substrate.

Third Embodiment

In this embodiment, one embodiment of mixture or agitation of two and more kinds of liquid, which is one of the operations necessary for the chemical reaction, will be shown.

Figure 3:
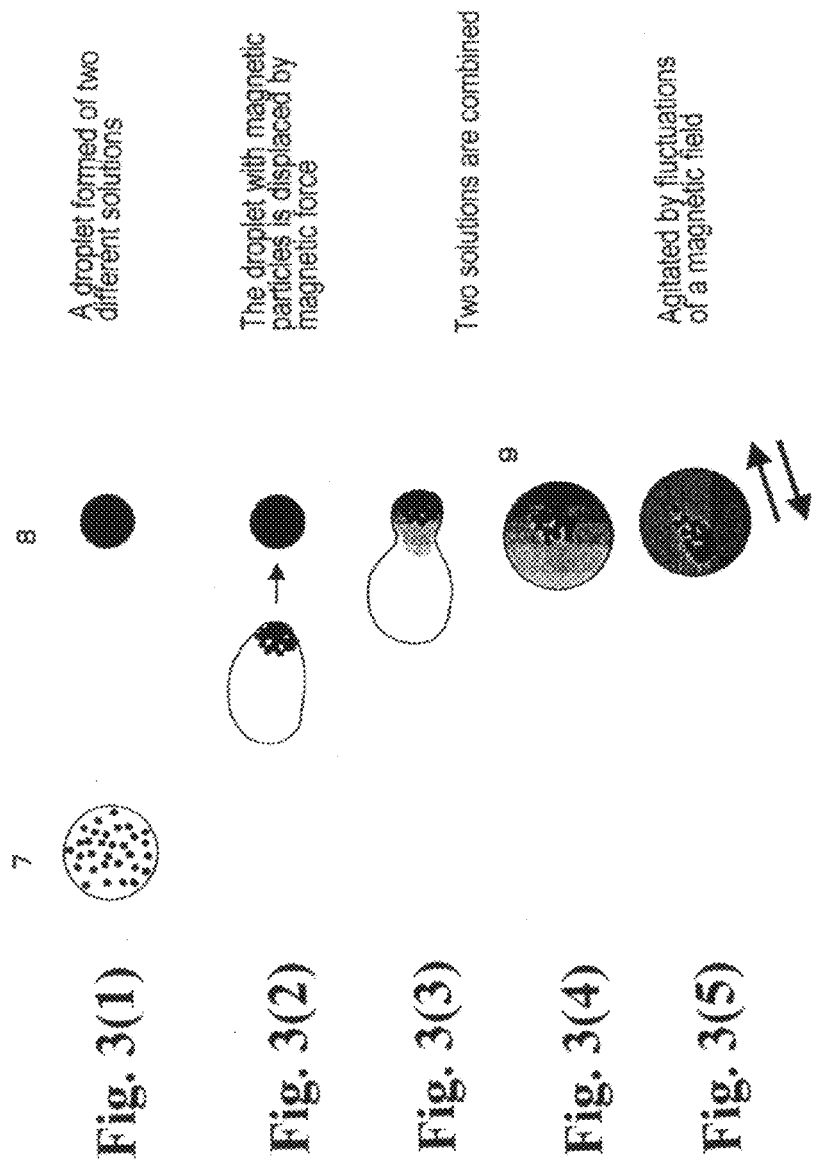
FIGS. 3(1)-3(5) are drawings showing processes of an example of mixture and agitation of two different kinds of liquid according to the invention, which will be explained in the third embodiment.

FIGS. 3(1)-3(5) show a process of mixture of two different kinds of liquid. In FIG. 3(1), a droplet 7 on the left side is a droplet including magnetic silica beads (adjusted in the first embodiment, and shown with the black spots inside the droplet), and a droplet 8 on the right side is a droplet including solution which does not include the magnetic silica beads and differs from the droplet 7. The droplet 7 is guided to the droplet 8 on the right side by the fluctuations of the magnetic field, and both the droplets 7 and 8 are blended (FIGS. 3(2), 3(3), 3(4)). Additionally, by an amplitude motion of the magnetic body particles inside a blended droplet 9 due to a magnetic force, this can be a substitute for a stirrer. By using the characteristic of the above-mentioned phenomenon, the mixture and agitation of the different liquid can be conducted.

Fourth Embodiment

In this embodiment, one embodiment conducting the preparative isolation and dilution of the liquid, which is one of the operations necessary for the chemical reaction, will be shown.

Figure 4:
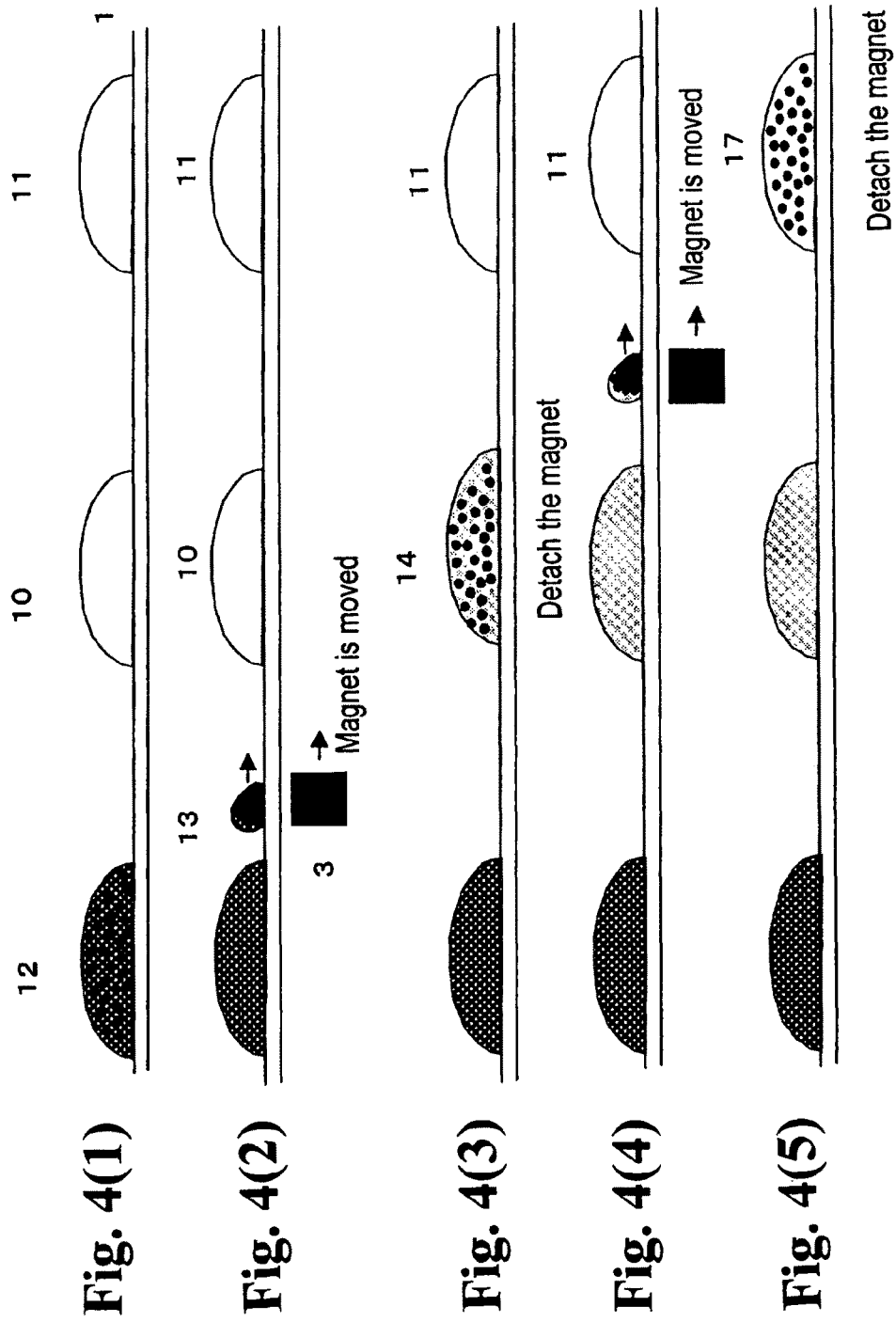
FIGS. 4(1)-4(5) are drawings showing processes of an example of preparative isolation and dilution methods of the liquid according to the invention, which will be explained in the fourth embodiment.

FIGS. 4(1)-4(5) show processes of preparative isolation and dilution operations of the liquid. Droplets 10, 11 including purified water with the volume of 50 µL are formed in two places on the polypropylene substrate 1. A droplet 12 on the left side is a droplet of an xylenecyanol aqueous solution with 0.01 (w/v) % including the magnetic silica beads (adjusted in the first embodiment, and shown with the black spots inside the droplet) with 5 mg (dry)/mL of concentration and displays a black color (the actual solution color is blue). When a small droplet 13, separated from the left droplet 12 by the magnet 3 which is displaced in the horizontal direction in FIG. 4(2), is blended with the central droplet 10 which is the purified water, a part of the component of the left droplet is carried by the small droplet 13, and the central droplet becomes a droplet 14 with a light gray color diluted more than the concentration of the component of the left droplet. In FIG. 4(4), the small droplet 13 is additionally carried toward the right droplet 11 as mentioned above, so that the droplet 11 is diluted more than the center droplet and becomes a droplet 17 with a very light gray color. By repeating the above-mentioned processes, a serial dilution series can be created. This results in the preparative isolation of a specific quantity of liquid from the droplet body when the magnetic silica beads are separated from the droplet body as the small droplet. The volume of the small droplet cut out of the droplet body under the above-mentioned condition, is approximately 2.5 µL including the magnetic silica beads, and if the size of the droplet body is 20 µL or more, the volume of the small droplet to be cut out changes little regardless of the volume of the droplet body.

Fifth Embodiment

Figure 5:
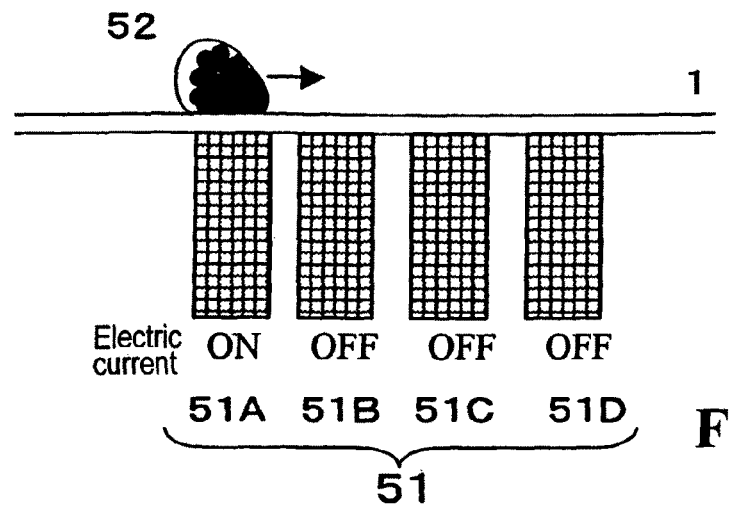
FIGS. 5(1)-5(3) are drawings showing processes of another example of the displacement method of the droplet according to the invention, which will be explained in the fifth embodiment.
Figure 5:
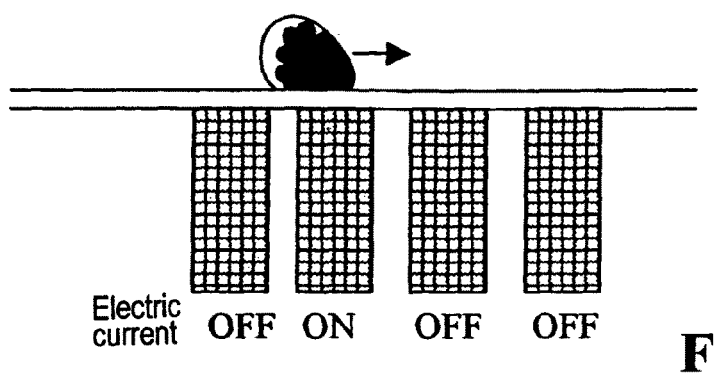
Figure 5:
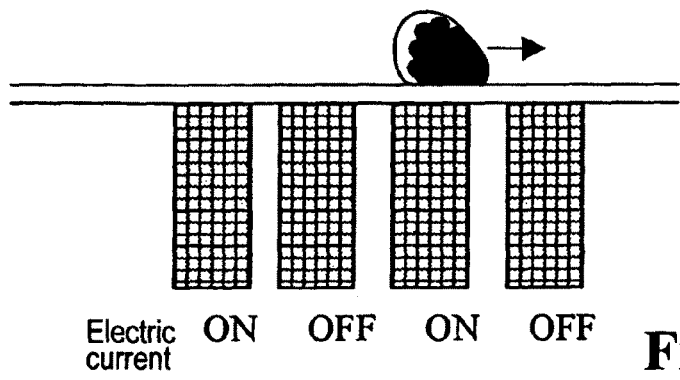

In the above-shown embodiments, the droplet is displaced by automatically moving the magnet on the lower side of the reaction substrate in a horizontal direction. However, even if electric magnets are placed in an array-like form, the droplet can be displaced. FIGS. 5(1), 5(2), 5(3) show a device using an electric magnet array and the displacement method of the droplet, and electric magnets 51 are arranged on the lower side of the reaction substrate 1 in the array-like form. In FIG. 5(1), the leftmost electric magnet 51A is applied current, and a droplet 52 including magnetic body particles is added on the surface of the reaction substrate 1. Next, when an electric current is applied to the second electric magnet 51B from the left and the first electric magnet 51A from the left is cut off the current, the droplet is displaced to the right direction (FIG. 5(2)). By applying the current to electric magnets 51C, 51D sequentially in the same way, the droplet can be displaced to the right direction (FIG. 5(3)). A control portion (not shown) conducts electric control to these electric magnets. As a result, the droplet can be displaced horizontally without any mechanical displacement of the magnet, so that the device can be downsized and contribute for a maintenance-free operation.

Figure 6:
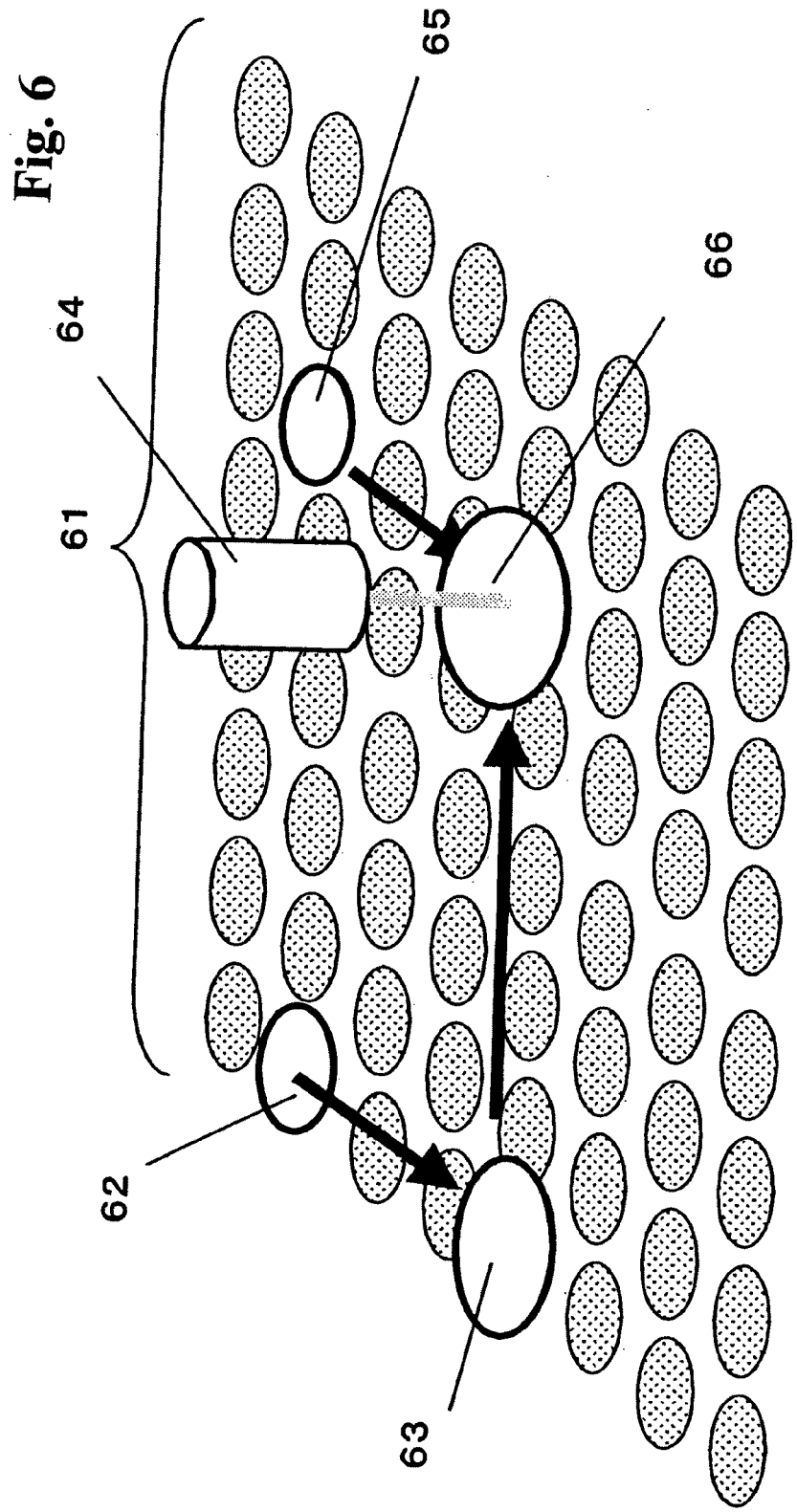
FIG. 6 is a drawing showing other example of the displacement method of the droplet according to the invention, which will be explained in the fifth embodiment.

By aligning the electric magnets in a reticular pattern, i.e. arranging in a matrix state, the displacement of the droplet can also be two-dimensionally developed. FIG. 6 shows a chemical reaction device wherein the electric magnets are placed in the matrix pattern, and a chemical reaction method using the above-mentioned device.

In FIG. 6, the reaction substrate (not shown) is placed on an electric magnet matrix 61, and three kinds of droplets are placed on the surface of the reaction substrate. The three kinds of droplets include, for example, reagents A, B, C respectively, and a chemical reaction wherein the reagents A, B are mixed; a mixture (A+B) and the reagent C are reacted with each other; and a reaction product detected by a detector, is conducted. First, a droplet 62 including magnetic body particles and the reagent A is displaced, blended with the droplet including the reagent B which is originally displaced, and becomes a reaction droplet 63 by the chemical reaction (mixture of the reagents A, B) by mixing. Next, the reaction droplet 63 is displaced up to the spot under a detector 64; a droplet 65 including the magnetic body particles and the reagent C is displaced to the spot under the detector 64 and blended into the reaction droplet 63; a second step of the chemical reaction by mixing is conducted; and as a reaction droplet 66, a reaction product is simultaneously detected at the detector 64.

As explained in the above, in the chemical reaction device and the chemical reaction method of the invention, fluid control elements such as a micro flow channel, a micro mixer, micropump and micro valve become unnecessary, so that the structure of the device can be remarkably simplified. Moreover, since multiple chemical reactions are conducted simultaneously on the same substrate, the invention can be applied to a Lab on a C hip device for combinatorial chemistry. Therefore, even in a design for a chemical reaction circuit, it is possible to develop a system with remarkably high flexibility.

Sixth Embodiment

The first to fifth embodiments show that the droplets located under the gas phase on the surface of the reaction substrate are displaced due to the fluctuations of the magnetic field. On the other hand, the displacement of the droplets of the invention can be conducted even in a state wherein the droplets exist inside a liquid phase such as oil and the like. Especially, in the chemical reaction including a heat process, a droplet operation inside the liquid phase becomes very effective due to the prevention of evaporation such as moisture from the droplets.

As a droplet inclusion medium used as the liquid phase, liquid materials which are in the aqueous solution forming the droplets, are preferred, and additionally, materials which do not interfere with the chemical reaction to be conducted, are preferred. As the above-mentioned materials, a carbon hydride type such as alkane; perfluoroalkane type; chemicals wherein a part of hydrogen atom of the alkane is fluorine; or liquid materials with water-insolubility or poor water-solubility such as mineral oil, silicone oil, fatty acid, fatty acid ester, fatty acid amide, fatty acid ketone, fatty acid amine and the like, can be cited.

Among the above-mentioned materials, a small material whose specific gravity is 1 and below, is preferably used. By using the small material whose specific gravity is 1 and below, the droplets sink inside the droplet inclusion medium, so that operability of the droplets due to the fluctuations of the magnetic field can be improved.

Also, among the above-mentioned materials, in a biochemical reaction at a high temperature such as the reaction using heat-resisting enzyme, materials with low volatility, more specifically, the mineral oil, silicone oil, fatty acid ester, fat and the like, whose boiling point is 200 degree and below, are effective. Even at high temperature, the droplet inclusion medium itself is not volatile, so that volatilization of the droplets can be prevented.

Among the above-mentioned materials, as the droplet inclusion medium, a material, having a melting point of a lower temperature than the temperature necessary for the chemical reaction to be conducted, is preferred. By using the material with the above-mentioned property, before the chemical reaction is conducted, the droplet inclusion medium is in a solid state and fixes the droplets in an arbitrary position; and when the chemical reaction is conducted, the droplets can be displaced in a droplet state of the droplet inclusion medium. As a result, before the reaction starts, the droplets necessary for the reaction store the reaction receptacle or the reaction substrate which are placed in the arbitrary position at the lower temperature than the melting point of the droplet inclusion medium. Therefore, the droplets can be prevented from being displaced in an undesirable direction. Also, when the reaction starts, the droplet inclusion medium is liquidized by humidification, so that the placed droplets can be displaced. For example, when the reaction receptacle or the reception substrate of the invention is supplied in the configuration of a microchip wherein an analytical reagent is incorporated as a clinical examination kit, a handling ability and stability during the storage time or transmit time, can be assured. In a microchemical chip, supply of a reaction reagent is also a problem to be resolved; however, in the invention, an arbitrary amount of necessary reagents can be incorporated into the reaction receptacle or the surface of the reception substrate beforehand as the droplets. Also, when the reaction circuit is designed on the chip, the reagent droplet necessary for the reaction can be fixed in an arbitrary position on the chip, so that various designs for reactions are possible.

For example, in the case of the reaction substrate shown in FIG. 6, the three kinds of droplets including the respective reagents A, B, C are placed inside a layer of the droplet inclusion medium on the surface of the reaction substrate; preserved at a temperature lower than the melting point of the droplet inclusion medium; and fixed. At the time of the chemical reaction, the droplet inclusion medium is melted, and in a state wherein the droplet can be displaced, the chemical reaction can be conducted.

More preferably, by using the material whose melting point is a room-temperature (15° C.~25° C.) as the droplet inclusion medium, the solidification can become possible at a general refrigerated temperature, and the reaction receptacle or the reaction substrate can be easily stored. For the above-mentioned material, specifically, normal alkane with approximately 16~23 of the number of carbon atoms can be cited. For example, octadecane which is alkane with 17 carbon chain numbers is normal alkane with the melting point around the room temperature.

Incidentally, when the droplet inclusion medium is melted, the periphery of the droplet becomes fluxional. However, by placing the droplet on a spot with a low water repellency partially on the surface of the reaction substrate; or including the magnetic body particles and magnetizing by a magnetic force from just underneath, a measure in order for the droplet not to be displaced until a reaction time can be possible.

The above-mentioned droplet inclusion medium is filled inside the reaction receptacle so that the droplet can exist in the droplet inclusion medium. When the reaction substrate is used, it is only required that the droplet inclusion medium contacts with the surface of the substrate in such a way as to be layered, and that the droplet exists inside the droplet inclusion medium. When the reaction substrate includes the wall surrounding the area which becomes the reaction field, the area surrounded by the wall can be confined by the droplet inclusion medium until at least the periphery of the droplet is covered.

Seventh Embodiment

Figure 7:
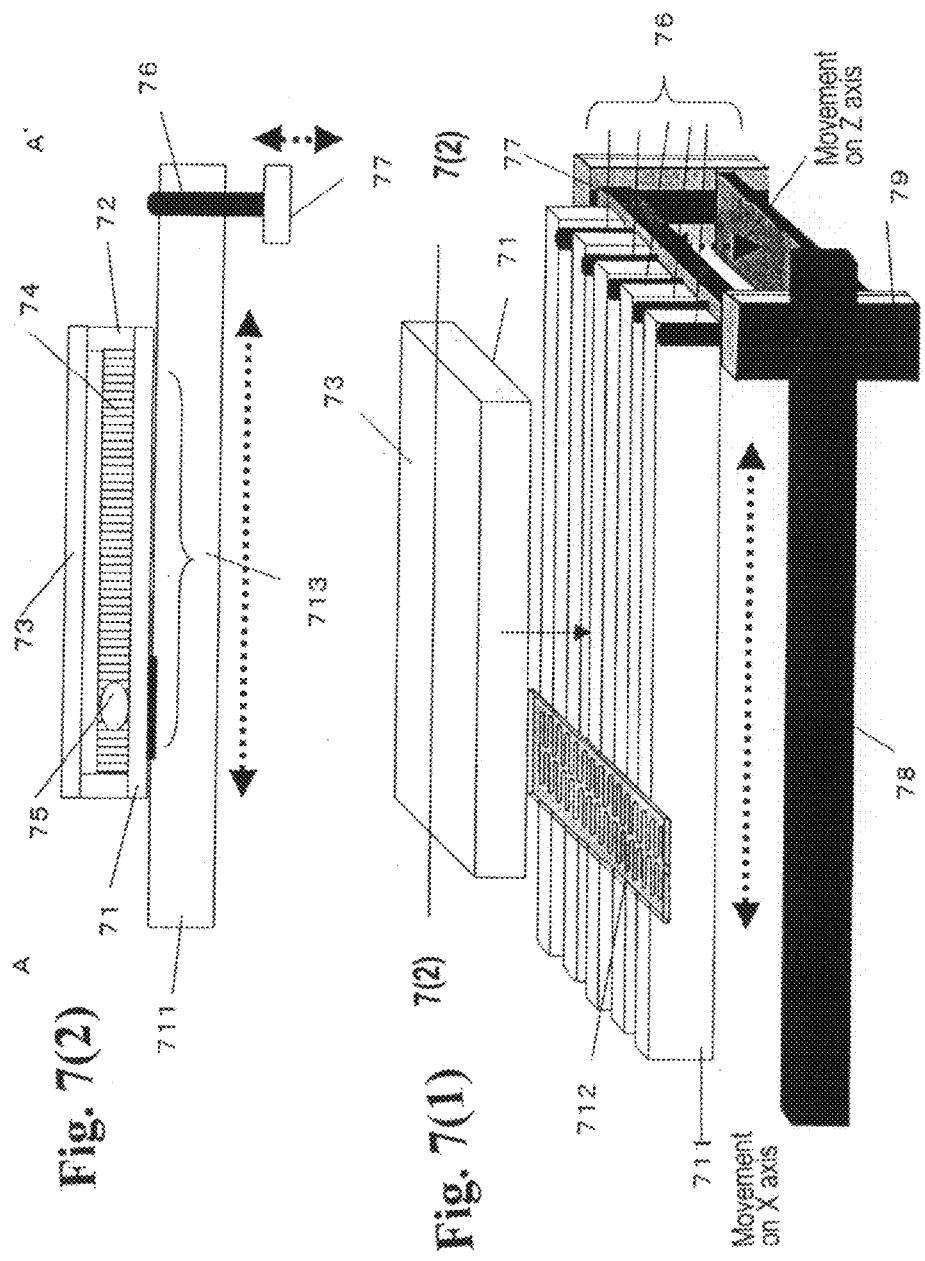
FIGS. 7(1), 7(2) are drawings showing an example of a device for conducting a temperature control of the droplet of the present embodiment, which will be explained in the seventh embodiment, and FIG. 7(1) is a perspective outline view and FIG. 7(2) is a vertical sectional view taken along line 7(2)-7(2)

In the embodiment, an example of a thermal control method such as heating and cooling of the liquid, which is one of the operations necessary for the chemical reaction, is shown. FIGS. 7(1), 7(2) show an example of the device. FIG. 7(1) is a perspective outline view of the device and FIG. 7(2) is a vertical sectional view taken along line 7(2)-7(2).

A reaction substrate 71 is a flat polypropylene plate of thickness 0.3 mm, 30 mm×90 mm, and in order to provide the closed-type reaction field on the surface of the substrate, a wall 72 with a height of 10 mm and a lid for a glass plate 73 with a thickness of 5 mm, are provided on the surface side of the flat plate. Silicone oil 74 is filled in the closed-type reaction field, so that the surface of the reaction substrate 71 contacts with the silicone oil, and a droplet 75 including the magnetic body particles exists inside the silicone oil. As a magnetic field applying means displacing the droplet by providing the fluctuations of the magnetic field to the droplet 75, a permanent magnet 76 and a displacement mechanism of the permanent magnet are provided. As the moving mechanism of the permanent magnet, a magnet support material 77 providing the permanent magnet 76; guides (x-axis guide 78, z-axis guide 79) for displacing the magnet support material in a two-dimensional direction; and a control portion (not shown) are provided. The magnet support material 77 wherein the permanent magnet 76 is provided is induced to a groove provided in the x-axis guide and the z-axis guide by the control of the control portion (not shown), and displaced in the two-dimensional direction. On a reaction substrate support material 711, a belt-like film heater 712 with a width of 10 mm is placed and set in a constant temperature by the control portion (not shown). The reaction substrate 71 is placed on the reaction substrate support material 711, so that the film heater 712 contacts with the lower surface of the reaction substrate 71, and a temperature variation area 713 can be formed on the surface of the reaction substrate 71. In the temperature variation area 713, a spot located just above the film heater 712 has the highest temperature, and as the distance from the film heater increases, the temperature continuously decreases.

Likewise, by placing one heat source on the bottom surface of the reaction receptacle or just under the reaction substrate, and producing heat at a constant temperature, the temperature variation area can be formed on the bottom surface of the reaction receptacle or on the surface of the reaction substrate. The temperature variation area includes a temperature gradient wherein a spot located just above the heat source has the highest temperature and whose temperature declines as the distance from the heat source increases. The droplet is displaced and placed in a spot with a temperature necessary for the chemical reaction to be conducted inside the temperature variation area due to the fluctuations of the magnetic field, so that soon after the above-mentioned droplet is placed, the liquid temperature of the droplet can be adjusted to the temperature of the above-mentioned spot. More specifically, even when the chemical reaction to be conducted requires the temperature variation, the liquid temperature can be promptly raised or lowered only by moving the droplet, and set in the appropriate temperature.

As for the temperature setting of the heating source, the temperature is set to be the highest temperature or higher for the chemical reaction to be conducted. Also, with one heating source, a cooling source such as a heat release plate or cooling fan may be provided on a low temperature side of the temperature gradient wherein a high temperature side is formed just above the heating source. By providing the cooling source, the temperature gradient formed inside the temperature variation area can be increased. As a result, the moving distance of the droplet can be narrowed, even if there are more than two different temperatures which are necessary for the chemical reaction to be conducted. Accordingly, an effective chemical reaction can be provided, and also, the reaction receptacle or the reaction substrate can be easily downsized.

In the embodiment, as the magnetic field applying means, the magnetic field applying means including the permanent magnet and the displacement mechanism of the permanent magnet is used. However, as shown in the fifth embodiment, the magnetic field applying means with a one-dimensional or two-dimensional electric magnet array and a control portion controlling energization of the electric magnet array, may be used.

Here, as the material of the reaction receptacle or the reaction substrate, a resin which can maintain a high contact angle with the droplet even at a high temperature, is preferably used. More specifically, polypropylene or a resin with the contact angle more than polypropylene, is preferred. When the surface of the glass or silicon has a water repellency treatment such as a silicon coating, it may possibly undermine the water repellency of the surface at the high temperature. However, this can be prevented by using the polypropylene reaction receptacle or reaction substrate. Moreover, since the resin has low thermal conductivity relative to the glass or silicon, it is possible to adjust a local temperature in a narrow area, and the temperature gradient formed inside the temperature variation area can be increased. This is effective for downsizing the reaction receptacle or the reaction substrate.

Eighth Embodiment

By using the chemical reaction device and reaction substrate shown in FIGS. 7(1), 7(2), as an example of the chemical reaction which requires heating, a PCR (Polymerase Chain Reaction) which is a typical nucleic-acid amplification reaction, is conducted. Conditions of the reaction substrate are the same conditions which are explained in the seventh embodiment. As the silicon oil layered on the reaction substrate, dimethylsilicon oil (manufactured by Shin-Etsu Chemical Co., Ltd., (KF-96-20cs), kinetic viscosity 20 $mm^2/s$ ($25°$ C.)) is used, and layered with a layer of a thickness 3 mm.

Compositions of the PCR reaction liquid forming the droplet (volume 3 μL) are potassium chloride of 50 mM; Tris-HCL buffer (pH 9.5) of 10 mM; magnesia chloride of 5 mM; PCR primer (Forward) for detecting beta-actine of 0.6 μM; PCR primer (Reverse) for detecting beta-actine of 0.6 μM manufactured by Applied Biosystems Co., Ltd.; heat-resistant DNA polymerase of 0.75 U manufactured by the Applied Biosystems Co., Ltd.; and Ex Taq DNA polymerase manufactured by Takara Shuzo Co., Ltd. Additionally, in order to prevent deactivation due to adsorption of DNA polymerase to the substrate surface and the magnetic body particles, bovine serum albumin of 0.2 (wt) % is added. A human standard genomic DNA purified product of 3 ng manufactured by the Applied Biosystems Co., Ltd.; and the magnetic silica beads (shown in the first embodiment) are added to the PCR reaction liquid, so that the concentration becomes 10 μg/μL in dry weight volume.

A heater current of the film heater is adjusted in such a way that the droplet located just above the film heater shows 99° C. In this way, the range of the temperature variation of the temperature variation area includes a range of annealing temperature and the denaturation temperature necessary at least for PCR.

In a program for a reaction cycle, first, the droplet including the PCR reaction liquid was rested for 2 seconds at a spot wherein the droplet inside the temperature variation area showed 95° C.; next, the droplet was rested for 2 seconds at a spot wherein the droplet inside the temperature variation area showed 60° C.; and the droplet was rested for 5 seconds at a spot wherein the droplet inside the temperature variation area showed 72° C. The above-mentioned processes are considered as one process in the above-mentioned order. This process was repeated 35 times while the droplet was displaced due to the fluctuations of the magnetic field. The amount of time necessary for the reaction was approximately 9 minutes. After the reaction was conducted, the presence or absence of a gene amplified product is examined by mean of 3% of agarose gel electrophoresis. A result showed the presence of a specific gene amplified product in a human beta actin gene.

The bovine serum albumin (BSA) added to the reaction liquid as described above is a blocking agent added in order to prevent for the enzyme from adsorbing to the surface of the resin substrate, the surface of a magnetic particle and the like, and besides the BSA, protein such as various kinds of albumin, gelatin (altered collagen), casein, polylysine and the like, and native or synthetic peptide were effective.

When the chemical reaction requiring a high temperature close to 100° C. such as a PCR reaction is conducted, the silicone oil with a kinetic viscosity between 5 mm$^2$/s and 100 mm$^2$/s (25° C.) is preferably used as the droplet inclusion medium. By using the silicone oil with the kinetic viscosity 5 mm$^2$/s or more, the droplet inclusion medium is not volatile even at the high temperature. Also, by using the silicone oil with the kinetic viscosity 100 mm$^2$/s or less, the displacement of the droplet due to the fluctuations of the magnetic field cannot be interfered.

In a usual thermal cycler for PCR, in order to cool down from heat denaturation (95° C.) to annealing (50~60° C.), a cooling device such as a Peltier element is required, and the time required for the amplification of a similar target gene is also required for more than an hour. However, in the invention, the reaction temperature can be controlled only by the displacement of the droplet on the temperature gradient. Moreover, due to the nature of a micro droplet of a microliter order, a capability for following a surrounding temperature is excellent, so that a high-speed PCR reaction can be conducted by a significantly simple device.

As the nucleic-acid amplification reaction of the invention, besides a PCR method (U.S. Pat. No. 4,683,195, U.S. Pat. No. 4,683,202, U.S. Pat. No. 4,800,159, and U.S. Pat. No. 4,965,188), an LCR method (U.S. Pat. No. 5,494,810); Q β method (U.S. Pat. No. 4,786,600); NASBA method (U.S. Pat. No. 5,409,818); LAMP method (U.S. Pat. No. 3,313,358); SDA method (U.S. Pat. No. 5,455,166); RCA method (U.S. Pat. No. 5,354,688); ICAN method (U.S. Pat. No. 3,433,929); TAS method (U.S. Pat. No. 2,843,586) can be used.

The composition of the reaction liquid required for the nucleic-acid amplification reaction and the reaction temperature can be selected accordingly by the person skilled in the art. The composition includes the magnetic body particles with the hydrophilic surfaces as described above and nucleic acid intended for the amplification. The droplet consisting of nucleic-acid amplification reaction liquid including materials necessary for the respective nucleic-acid amplification reaction, is placed in a spot wherein a droplet temperature is controlled to a required temperature for the nucleic-acid amplification reaction to be conducted for a required time by means of the fluctuations of the magnetic field. As a result, the nucleic-acid amplification reaction can be conducted within the droplet.

In the PCR method, LCR method, TAS method and the like, a thermal cycle requiring two to three conditions of temperatures which are distant with each other is required to be repeated more than once. However, in the invention, the amplification becomes possible only by repeating the displacement and placement of the droplet due to the fluctuations of the magnetic field in the spot wherein the droplet temperature is controlled to a required temperature within the temperature variation area including a temperature range necessary for each nucleic-acid amplification reaction.

Also, the SDA method, Q β method, NASBA method, ICAN method, ICAT method, RCA method are an isothermal amplification reaction under one condition of temperature within a range approximately between 37 and 65 degrees. Even in the isothermal amplification reaction, an optimum temperature differs according to an object for the amplification, so that the droplet is placed in the spot wherein the temperature of the droplet is controlled at the optimum temperature according to the subject template of the amplification, so that amplification efficiency can be improved.

Ninth Embodiment

Figure 8:
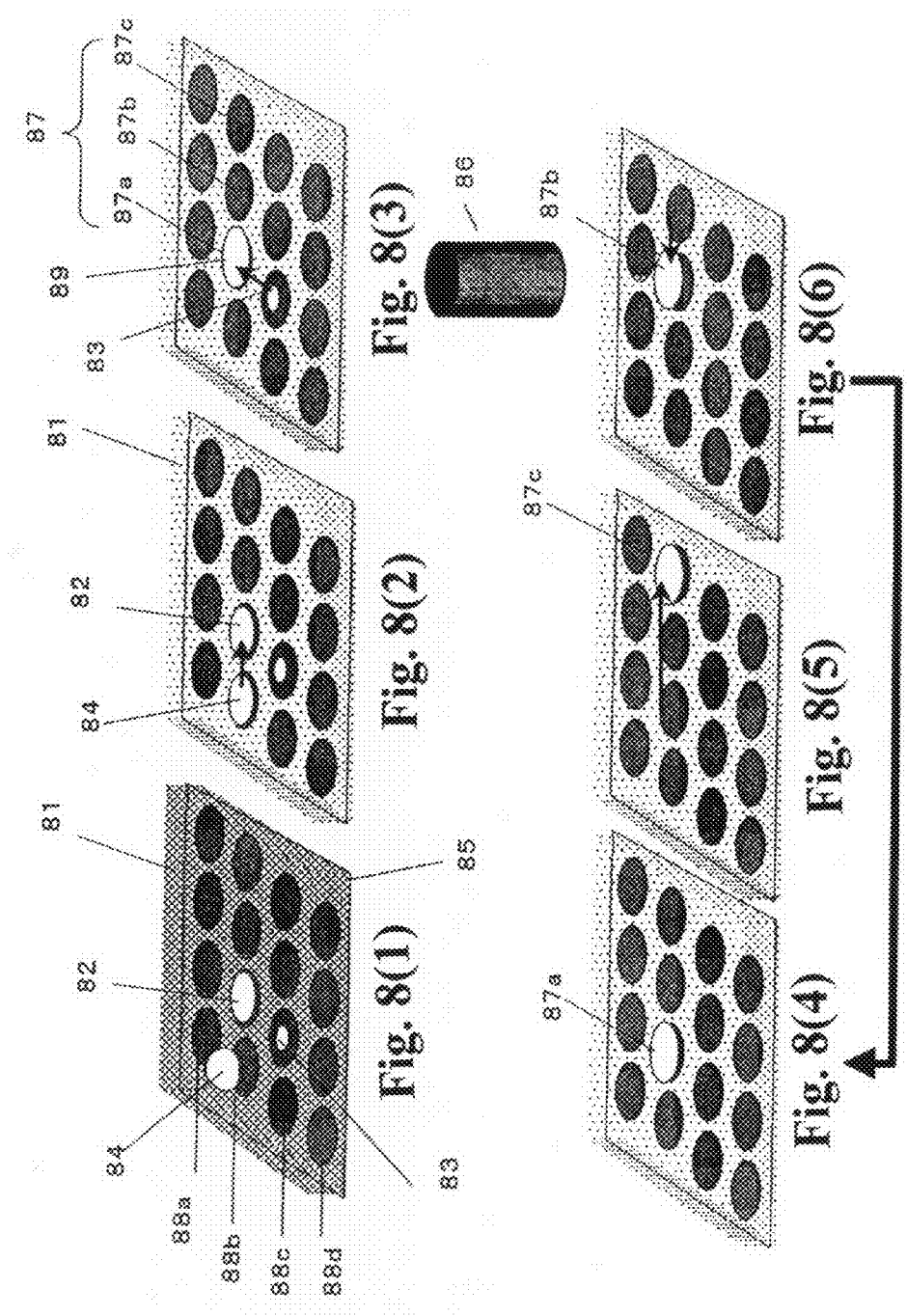
FIGS. 8(1)-8(6) are drawings showing another example of a nucleic-acid amplification device, which will be explained in the eighth embodiment; and processes of a nucleic-acid amplification reaction.

An object of this embodiment is conducting a real-time PCR detecting method, as a deformed example of the eighth embodiment. FIGS. 8(1)-8(6) show a device and a process of the real-time PCR method.

This embodiment is roughly the same as experimental conditions of the eighth embodiment. However, the gene amplified product is fluorometricly detected in the PCR reaction liquid in real time, so that a fluorochrome SYBR (registered trademark), Green I (Molecular Probe Co., Ltd.) is added in the dilution of twenty thousand times. Also, in order to prevent a non-specific reaction, a template DNA (human standard genomic DNA purified product) and the PCR reaction liquid except for the heat-resistant DNA polymerase are combined, and a hot start method wherein the liquid with the heat-resistant DNA polymerase are combined after the temperature is regulated at 95° C., is used. Also, paraffin whose melting point is near 30° C. is used as the droplet inclusion medium instead of the silicone oil. In order to set a reagent (the PCR reaction liquid except for the heat-resistant DNA polymerase, and the heat-resistant DNA polymerase) necessary for the reaction in the reaction substrate beforehand, each reagent liquid is delivered by drops into a place wherein the paraffin is liquid at a temperature of 40 degrees of the reaction substrate, and placed at an arbitrary spot as each reagent droplet. An experiment was started in a state wherein the substrate in which once the paraffin had placed was fixed inside a refrigerator. Also, in the device, as the magnetic field applying means, the magnetic field applying means using the two-dimensional electric magnet array is used.

FIG. 8(1) shows a state wherein a droplet 82 including the PCR reaction liquid except for the heat-resistant DNA polymerase and a droplet 83 including the heat-resistant DNA polymerase are embedded in paraffin within a solidified paraffin layer 81. Also, it shows a state wherein a reagent droplet 84 including the template DNA is placed. In this state, the reagent droplet 84 is located on the solidified paraffin layer, and not settled on the surface of a substrate 85. Incidentally, a group of spots indicated by 88a~88d shows positions of the electric magnets configuring the electric magnet array.

In FIG. 8(2), the reaction substrate 85 is placed at the temperature of 40 degrees, so that the paraffin layer 81 is liquefied, and the reagent droplet 84 is settled on the surface of the substrate and blended with the droplet 82 including the PCR reaction liquid except for the heat-resistant DNA polymerase by a magnetic force.

In a process in FIG. 8(3), a temperature variation area 87 including a temperature range required for the PCR is formed on the reaction substrate 85 by an external heating source (not shown). More specifically, the temperature variation area 87 includes a spot 87a wherein the droplet is heated to a denaturation temperature (for example, 95° C.) of the template nucleic acid; a spot 87b wherein the droplet is heated to an elongation reaction temperature (for example, 72° C.) of the template nucleic acid; and a spot 87c wherein the droplet is heated to an annealing temperature (for example, 50° C.) of a primer to the template nucleic acid.

First, a droplet 89 wherein the above-mentioned reagent droplet 84 and the droplet 82 including the PCR reaction liquid are blended, is heated to 95° C. at the spot 87a, so that the template DNA inside the sample is denatured and put into a single strand. In this place, the prepared droplet 83 including the heat-resistant DNA polymerase is displaced, so-called a hot start PCR is established. Incidentally, the right timing for blending the droplet including the heat-resistant DNA polymerase may be in an elongation reaction process in FIG. 8(6) wherein the enzyme is active.

The denatured template DNA through the processes in FIGS. 8(3), 8(4) is transferred to an annealing process in FIG. 8(5). The time required for the displacement of the droplet for 12 mm between the spots 87a and 87c of the substrate was approximately two seconds under conditions of this embodiment. Next, in the process in FIG. 8(6), the droplet is placed in the spot 87b at a temperature of 72° C. which is the optimum temperature of a polymerase reaction; the elongation reaction is conducted; and one cycle of the PCR reaction is completed. Then, the droplet is returned to the spot 87a shown in the process in FIG. 8(4), and a next cycle from a heat denaturation process starts. In this process, 25 to 40 cycles of gene amplifications are repeated. However, a fluorescence signal from the SYBR Green I is monitored by a fluorescence detector 86 at each cycle in the position on the substrate in FIG. 8(6), so that a gene amplification signal can be observed in real time.

Moreover, after the PCR reaction is completed, the droplet is trapped at a fluorescence detection position, and the change of the fluorescence signal is observed by changing the temperature in stages, so that data of a melting curve of the amplified DNA can be also obtained. These functions are general functions of a real-time PCR device which is commercially available now. However, due to the invention, the design of a gene analysis device with a compact and simple mechanism became available.

Tenth Embodiment

The nucleic acid is selectively adsorbed into the magnetic body particles with the hydrophilic surfaces used in the invention, especially into the magnetic body particles whose surfaces include the silica, so that the nucleic acid can be extracted from a sample including the nucleic acid inside the same reaction receptacle or on the surface of the reaction substrate, and moreover, can be purified. Also, after the nucleic acid is extracted or after the nucleic acid is extracted and purified, the nucleic acid can be provided for the further chemical reaction, for example, the nucleic-acid amplification reaction which was explained in the eighth and ninth embodiments inside the same reaction receptacle or on the surface of the reaction substrate. More specifically, a droplet including nucleic-acid extraction liquid for extracting the nucleic acid from the material including the nucleic acid; a droplet including cleaning liquid of the magnetic body particles wherein the nucleic acid was attached according to the needs; and a droplet including releasing fluid for releasing the nucleic acid adsorbed to the magnetic body particles, are placed inside the same reaction receptacle or on the surface of the reaction substrate. The nucleic acid is displaced among each droplet with the displacement of the droplet including the magnetic body particles due to the fluctuations of the magnetic field as a displacement medium of the magnetic body particles. As a result, the reaction (extraction and purification of the nucleic acid in the sample) inside each droplet can be conducted.

Here, regarding extracting and purifying methods of the nucleic acid using the magnetic body particles in the sample including the nucleic acid, a Japanese Unexamined Patent Publication (TOKKAI) No. H2-289596 can be referred.

The sample including the nucleic acid (hereinafter may be called a nucleic acid-containing sample) is not specially limited as long as the sample includes the nucleic acid, and a body-derived sample such as tissues of plants and animals, body fluids, excretory substance and the like; and a nucleic acid-containing body such as a cell, protozoa, fungus, bacterium, virus and the like, can be cited. The body fluids include blood, spinal fluid, saliva and milk, and the excretory substance includes feces, urine and sweat, and the above-mentioned substances may be combined. The cell includes a white cell and platelet in the blood, and these may be combined.

As the nucleic-acid extraction liquid for extracting the nucleic acid from the material including the nucleic acid, buffer solution including a chaotropic material, EDTA, Tris-HCL and the like, can be cited. As the chaotropic material, guanidinium hydrochloride, guanidine isothiane acid chloride, potassium iodide, urea and the like can be cited.

As the magnetic body particles used for adsorbing the nucleic acid, any magnetic body particles can be used as long as the magnetic body particles include the surfaces which can selectively adsorb the nucleic acid, and besides the magnetic body particles including silica on the surfaces of the magnetic body particles, the magnetic body particles including anion-exchange resin may be used.

As the cleaning liquid which cleans the magnetic body particles wherein the nucleic acid is adsorbed, any cleaning liquid may be used as long as the cleaning liquid can melt another fraction which is included in the nucleic acid-containing sample such as protein glucide and the like or the component of the reagent which is included in the nucleic-acid extraction liquid while the nucleic acid is adsorbed into the surfaces of the magnetic body particles. As a specific example, a high-salt aqueous solution such as sodium chloride, potassium chloride, ammonium sulfate and the like, and an alcohol aqueous solution such as ethanol, isopropanol and the like can be used.

As the releasing fluid for releasing the nucleic acid adsorbed to the magnetic body particles, water or the buffer solution including low-concentrated salt can be used. More specifically, tris buffer solution, phosphate buffer solution, distilled water and the like can be used.

Figure 9:
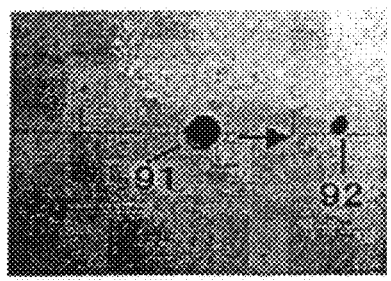
FIGS. 9(1)-9(10) are drawings showing extracting and purifying processes of nucleic acid using magnetic body particles from a sample including the nucleic acid, which will be explained in the ninth embodiment.
Figure 9:
Figure 9:
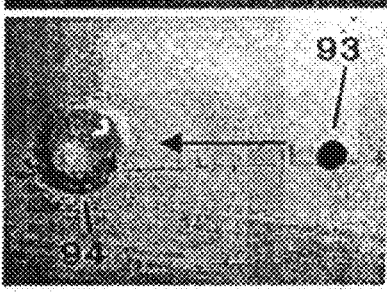
Figure 9:
Figure 9:
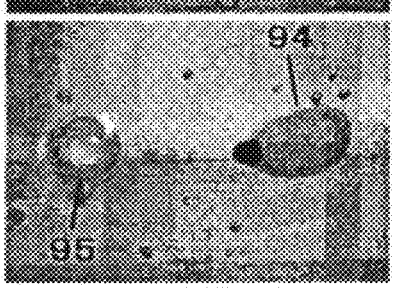
Figure 9:
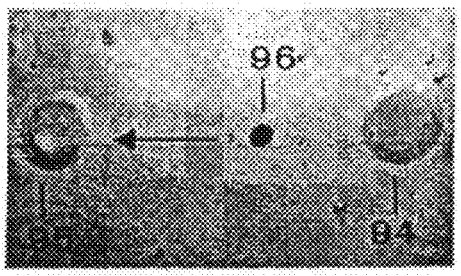
Figure 9:
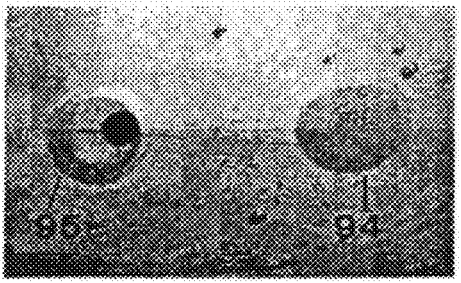
Figure 9:
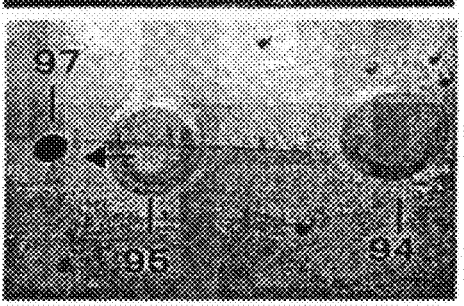
Figure 9:
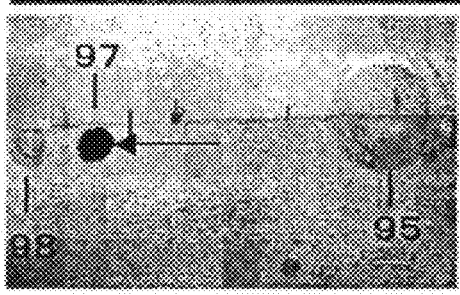
Figure 9:
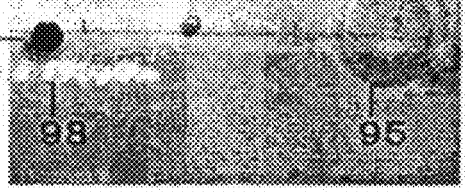

FIGS. 9(1) to 9(10) show results of the embodiments wherein the nucleic acid is extracted from a blood sample using the magnetic silica beads, purified, and observed from the upper side of a substrate surface side.

On the surface of a Teflon reaction substrate, a dimethylsilicon oil (used in the eight embodiment) layer is formed. In the dimethylsilicon oil layer, the droplet including the nucleic-acid extraction liquid; the droplet including the cleaning liquid of the magnetic body particles; and the droplet including the PCR reaction liquid, are prepared. On the lower side of the reaction substrate, the permanent magnet is prepared, and by displacing the permanent magnet in a direction of an arrow in the figures, the fluctuations of the magnetic field are provided to the droplets. As explained later, the droplet including the magnetic body particles is displaced or the small droplet including the magnetic body particles is separated from the droplet body.

A droplet 91 (5 µL) including the nucleic-acid extraction liquid consists of a 2M guanidine isocyanate aqueous solution, and includes the magnetic silica beads of 100 mg (dry)/ml (adjusted in the first embodiment) (FIG. 9(1)). A droplet 92 of the blood sample (0.3 µL) is separately prepared, and due to the fluctuations of the magnetic field, the droplet 91 including the nucleic-acid extraction liquid and the droplet 92 of the blood sample are blended, so that a droplet 93 is produced (FIG. 9(2)). Inside the droplet 93, the nucleic acid is adsorbed into the magnetic silica beads and extracted. After that, the droplet 93 is blended in a droplet 94 (50 µL) including the cleaning liquid (10 mM tris-hydrochloric acid buffer solution, pH 8.0) of the magnetic body particles wherein the nucleic acid is adsorbed. The magnetic silica beads wherein the nucleic acid is adsorbed inside the droplet are cleaned and the nucleic acid is purified (FIG. 9(4)).

After the magnetic silica beads are cleaned, a small droplet 96 including the magnetic silica beads is separated from the first droplet 94 including the cleaning solution (FIGS. 9(5), 9(6)); and blended with a second droplet 95 (50 μL) including the cleaning solution (the composition is the same as the droplet 94); and the magnetic silica beads are cleaned repeatedly (FIG. 9(7)). When the small droplet including the magnetic silica beads is separated from the droplet including the cleaning solution, the magnet placed on the lower side of the reaction substrate is displaced as follows. The magnet is moved close to the droplet in such a way that the magnetic silica beads spread to the droplet consisting of the cleaning solution are gathered inside the droplet. After the magnetic silica beads are gathered inside the droplet, the body of the magnetic silica beads is pulled over to the interface of the droplet, and the displacement speed of the magnet is increased, so that the body of the magnetic silica beads is separated with some amount of surrounding cleaning solution.

A droplet 97 including the magnetic silica beads after the second-time cleaning process is blended in a droplet 98 including the PCR reaction liquid. Here, the PCR reaction liquid functions as the releasing fluid of the nucleic acid adsorbed to the magnetic body particles, and the nucleic acid is released into the PCR reaction liquid. After that, as explained in the eight or ninth embodiment, the droplet including the PCR reaction liquid is displaced and placed in a position at a temperature necessary for the PCR inside the temperature variation area of the reaction substrate, so that the amplification reaction can be conducted.

Incidentally, extracting and purifying processes of the nucleic acid from the sample including the nucleic acid are not limited to processes shown in FIGS. 9(1) to 9(10).

After the nucleic acid is extracted, the small droplet including the magnetic body particles wherein the nucleic acid is adsorbed is separated from the droplet including the nucleic-acid extraction liquid, and then the small droplet may be blended in the droplet including the cleaning liquid. The number of times of the cleaning of the magnetic body particles wherein the nucleic acid is adsorbed can be accordingly changed as long as there would cause no inhibition against the nucleic-acid amplification reaction which is the subsequent process. Also, if there is no inhibition against the nucleic-acid amplification reaction, the cleaning process can be omitted.

As shown in the embodiments, by using the magnetic body particles as a displacement medium of the nucleic acid, the preparation of the sample including the nucleic acid can be also conducted in the same reaction receptacle or the surface of the reaction substrate. For example, a droplet for culture consisting of culture fluid is formed in the reaction receptacle or the surface of the reaction substrate; and E. coli with plasmid wherein an arbitrary gene is cloned is implanted in the droplet for the culture, incubated in a 37° C. environment, and proliferated. After that, the multiplied E. coli are blended in the droplet consisting of lysis solution which becomes the nucleic-acid extraction liquid, and a plasmid DNA is adsorbed to the surfaces of the magnetic body particles. At this moment, the magnetic body particles may be included in either one of the droplets including the droplet for the culture or the droplet including the lysis solution.

After that, in the following analyzing process, for example, the droplet is added with a third droplet including Sanger reaction reagent for decoding a base sequence, and a sequencing reaction is conducted. As a result, an electrophoresis sample for decoding the cloned base sequence can be prepared in the same reaction receptacle or on the surface of the reaction substrate.

Even in the embodiments, at least one droplet placed in the reaction receptacle or on the surface of the reaction substrate is preferred to be confined in the droplet inclusion medium like the sixth embodiment. Moreover, the droplet inclusion medium is preferred to be the material having the melting point of the lower temperature than the temperature necessary for the chemical reaction to be conducted. As a result, the reaction receptacle or the reaction substrate according to the invention can be provided as a portable device for conducting the nucleic-acid amplification reaction from the sample including the nucleic acid. As such a portable reaction receptacle or reaction substrate, more specifically, at least the droplet including the nucleic-acid extraction liquid and the droplet including the nucleic-acid amplification reaction liquid are enclosed in the droplet inclusion medium in the solid state beforehand. Moreover, the droplet including the cleaning liquid of the magnetic body particles is enclosed according to the needs. As the droplet including the nucleic-acid amplification reaction liquid, as explained in the ninth embodiment, in order to conduct the hot start method, the heat-resistant polymerase may be prepared as another droplet. When the reaction is conducted, from the inside of the reaction receptacle or the outside of the reaction substrate, the sample including the nucleic acid is input by an arbitrary method such as a divided injection by a syringe, and the nucleic-acid amplification can be conducted inside the reaction receptacle or on the surface of the reaction substrate from the extraction of the nucleic acid.

The disclosure of Japanese Patent Application No. 2006-188708, filed on Jul. 7, 2006, is incorporated in the application.

While the invention has been explained with reference to the specific embodiments of the invention, the explanation is illustrative and the invention is limited only by the appended claims.

What is claimed is:

1. A chemical reaction method for conducting a chemical reaction in a fluid of a droplet inside a reaction receptacle or on a surface of a reaction substrate, comprising the steps of:
    providing fluctuations of a magnetic field to the droplet including an aqueous solution having magnetic body particles with a hydrophilic surface,
    transmitting a physical force to the aqueous solution through the magnetic body particles, moving the droplet by the physical force, and conducting an operation necessary for a chemical reaction,
    wherein the reaction receptacle or the reaction substrate comprises a temperature variation area in which a temperature changes continuously, the droplet being moved to at least one spot inside the temperature variation area by the fluctuations of the magnetic field, and the chemical reaction is conducted by controlling temperature of the droplet,
    wherein the droplet further comprises nucleic acid for a nucleic acid amplification, the temperature variation area has a temperature necessary at least for a nucleic-acid amplification, and the nucleic acid amplification is conducted by moving the droplet to a spot in the temperature variation area controlled to keep at least one temperature necessary for the nucleic-acid amplification,
    wherein the nucleic acid is attached to surfaces of the magnetic body particles by contacting the magnetic body particles with the hydrophilic surfaces with a sample including the nucleic acid inside the droplet having nucleic-acid extraction liquid for extracting the nucleic acid from the sample, wherein a droplet inclusion medium is filled in the reaction receptacle or contacted with the surface of the reaction substrate in such a way as to be layered, said droplet inclusion medium is insoluble in the aqueous solution forming the droplet, the droplet is confined in the droplet inclusion medium, and the droplet contacts a surface of a wall inside the reaction receptacle or the reaction substrate and is displaced due to the fluctuations of the magnetic field, and wherein the droplet inclusion medium has a melting point lower than a temperature for conducting the chemical reaction, the droplet inclusion medium is in a solid state and fixes the droplet before conducting the chemical reaction, and the droplet inclusion medium is in a liquid state and enabling the droplet to move when the chemical reaction is conducted.

2. A chemical reaction method according to claim 1, wherein the nucleic acid attached to the surfaces of the magnetic body particles is cleaned inside the droplet including cleaning liquid of the magnetic body particles.

3. A chemical reaction method according to claim 1, wherein the droplet includes a first droplet having a PCR reaction liquid except for a heat-resistant DNA polymerase, a second droplet including the heat-resistant DNA polymerase, and a reagent droplet, each having the magnetic body particles therein and being placed in the droplet inclusion medium.

4. A chemical reaction method according to claim 3, wherein the droplet inclusion medium is at first melted by heating, and then, the first droplet, the second droplet and the reagent droplet are moved to conduct the chemical reaction.

* * * * *